(12) United States Patent
Semba et al.

(10) Patent No.: US 6,709,847 B2
(45) Date of Patent: Mar. 23, 2004

(54) IMMOBILIZED EUPHORBIACEAE, POACEAE OR OLACAEAE S-HYDROXYNITRILE LYASE

(75) Inventors: Hisashi Semba, Ibaraki (JP); Yukio Dobashi, Ibaraki (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/758,317

(22) Filed: Jan. 12, 2001

(65) Prior Publication Data

US 2002/0064840 A1 May 30, 2002

(30) Foreign Application Priority Data

Jan. 12, 2000 (JP) ........................................ 2000-003386

(51) Int. Cl.$^7$ ................................................ C12P 13/00
(52) U.S. Cl. ........................ 435/128; 435/176; 435/280
(58) Field of Search ................................. 435/128, 176, 435/280

(56) References Cited

U.S. PATENT DOCUMENTS

| | | | |
|---|---|---|---|
| 5,177,242 A | | 1/1993 | Andruski et al. ............ 558/351 |
| 5,885,809 A | * | 3/1999 | Effenberger ................ 435/128 |

OTHER PUBLICATIONS

K. Trummler & H. Wajant, "Molecular cloning of acetone cyanohydrin lyase from flax (*Linum usitatissimum*)," *J. Biol. Chem.*, 272(8): 4770–4 (1997).

H. Wajant & F. Effenburger, "Hydroxynitrile lyases of higher plants," *Biol. Chem.*, 377:611–7 (1996).

M. Suelves & P. Puigdomènech, "Molecular cloning of the cDNA coding for the (R)–(+)–mandelonitrile lyase of *Prunus amygdalus*: temporal and spatial expression patterns in flowers and mature seeds," *Planta*, 206: 388–93 (1998).

I–P. Cheng & J.E. Poulton, "Cloning of cDNA of *Prunus serotina* (R)–(+)–mandelonitrile lyase and identification of a putative FAD–binding site," *Plant Cell Physiol.*, 34(7): 1139–43 (1993).

H. Lauble et al., "Crystallization and preliminary X–ray diffraction studies of mandelonitrile lyase from almonds," *Proteins: Sruct., Funct., Genet.*, 19: 343–7 (1994).

R.A. Messing, "Adsorption and inorganic bridge formations," *Methods in Enzymology*, 44: 148–161 (1976).

Hughes, J. et al., "Purification, Characterization, and Cloning of α–Hydroxynitrile lyase from Cassava (*Manihot esculenta* Crantz)," *Arch. Biochem. Biophys.* 311(2): 496–502 (1994).

Wajant, H. et al., "Acetone Cyanohydrin Lyase from *Manihot esculenta* (Cassava) is Serologically Distinct from other Hydroxynitrile Lyases," *Plant Sci.* 108: 1–11 (1995).

Seely, M.K. et al., "The Metabolism of Aromatic Compounds in Higher Plants VIII: On the Requirement of Hydroxynitrile Lyase for Flavin," *J. Mol. Biol.* 241(19): 4457–62 (1966).

Wajant, H. & Pfizenmaier, K., "Identification of Potential Active–site Redidues in the Hydroxynitrile Lyase from *Manihot esculenta* by Site–directed Mutagenesis," *J. Biol. Chem.*, 271(42): 25830–34 (1996).

E. Wehtje, et al. "Formation of C–C bonds by mandelonitrile lyase in organic solvents" *Biotechnology and Bioengineering* 36: 39–46 (1990).

E. Wehtje, et al. "Activity and operational stability of immobilized mandelonitrile lyase in methanol/water mixtures" *Appl. Microbiol. Biotechnol.* 29: 419–425 (1988).

E. Wehtje, et al. "Improved activity retention of enzymes deposited on solid supports" *Biotechnology and Bioengineering* 41: 171–178 (1993).

\* cited by examiner

*Primary Examiner*—Irene Marx
(74) *Attorney, Agent, or Firm*—Finnegan, Henderson, Farabow, Garrett & Dunner

(57) ABSTRACT

The present invention relates to a method for synthesizing optically active cyanohydrin. An immobilized enzyme is used in the invention, in which (S)-hydroxynitrile lyase is immobilized in a carrier comprising a porous inorganic material.

12 Claims, 3 Drawing Sheets

# IMMOBILIZED EUPHORBIACEAE, POACEAE OR OLACAEAE S-HYDROXYNITRILE LYASE

FIELD OF THE INVENTION

The present invention relates to an immobilized enzyme in which (S)-hydroxynitrile lyase is immobilized in an immobilization carrier with a high absorption ratio (or adsortion ratio), a method for producing said immobilized enzyme, and a method for producing optically active cyanohydrin using said immobilized enzyme.

BACKGROUND OF THE INVENTION (S)-hydroxynitrile lyase is useful as an enzyme for synthesizing optically active cyanohydrins. In organic solvent reaction systems which are ordinarily used enzymatic synthesizing of the compounds, the enzyme are used, for example, as immobilized enzymes for dispersing the enzyme in the reaction system and for performing the reaction effectively. As an example in which (S)-hydroxynitrile lyase was immobilized, the immobilization to a micro cellulose powder and nitrocellulose has been reported. However, these cellulosic carriers have a low absorption ratio of the enzyme, arising inconveniences such that enormous amounts of carriers are necessary to immobilize the enzyme required for the reaction.

The object of the present invention is to provide an immobilized enzyme in which (S)-hydroxynitrile lyase is immobilized in an immobilization carrier at a high absorption ratio, a method for producing said immobilized enzyme, and a method for producing optically active cyanohydrin using said immobilized enzyme.

The inventors of the present invention have studied extensively and intensively to solve above problems and have now found that (S)-hydroxynitrile lyase could be immobilized at high absorption ratio by use of a porous inorganic carrier such as a sintered clay carrier, a silica carrier, an alumina carrier, and a silica alumina carrier as an immobilization carrier for enzyme, thereby completing the present invention.

The present invention relates to an immobilized enzyme in which (S)-hydroxynitrile lyase is immobilized in a carrier comprising a porous inorganic material (e.g. the sintered clay carrier, the silica carrier, the alumina carrier, or the silica alumina carrier, having a pore size of 10–80 nm). (S)-hydroxynitrile lyase used herein can be derived from a plant of Euphorbiaceae, Poaceae(Gramineae) or Olacaceae.

The present invention also relates to a method for producing the immobilized enzyme in which (S)-hydroxynitrile lyase is immobilized in a carrier comprising a porous inorganic material (e.g. the sintered clay carrier, the silica carrier, the alumina carrier or the silica alumina carrier, having the pore size of 10–80 nm). (S)-hydroxynitrile lyase used herein can be derived from a plant of Euphorbiaceae, Poaceae(Gramineae) or Olacaceae.

The present invention further relates to a method for producing an optically active cyanohydrin, comprising bringing said immobilized enzyme into contact with a carbonyl compound and a cyanogen compound in the presence of a slightly water-soluble or water-insoluble organic solvent. The immobilized enzyme used herein may be collected to be reused from the reaction mixture.

The present invention will be described in detail as follows.

DETAILED DESCRIPTION OF THE INVENTION

Figure 1:
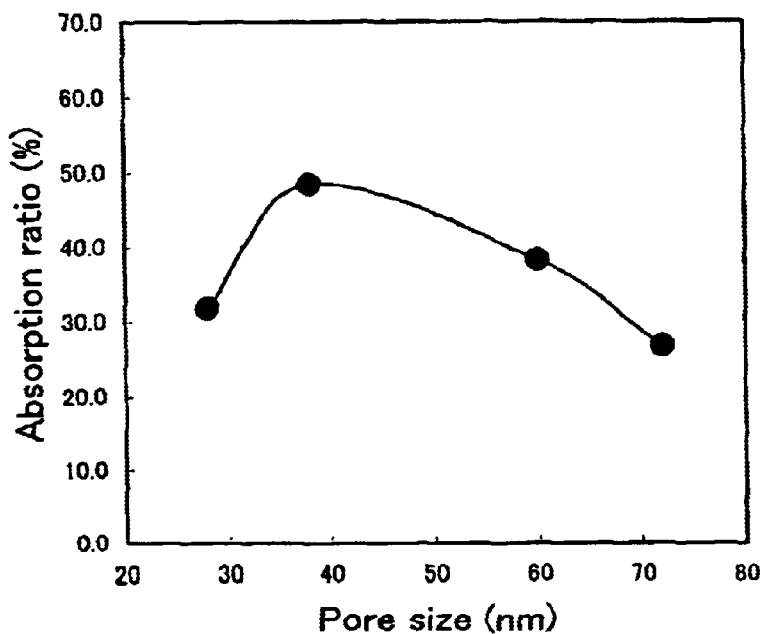
FIG. 1 shows the effect of the pore size of an immobilization carrier on the absorption ratio of enzyme in the case where Toyonite 200 is used as the carrier.

The present invention relates to an immobilized enzyme in which (S)-hydroxynitrile lyase is adsorbed in a carrier comprising a porous inorganic material. The immobilized enzyme of the invention is characterized in that absorption ratio of the enzyme in the carrier is higher than that of the conventional immobilized enzyme in which the enzyme is adsorbed on a cellulosic carrier. Thus, the immobilized enzyme of the invention has a remarkably high absorption ratio on the immobilization carrier. This immobilized enzyme can be produced as below.

1. Preparation of (S)-hydroxynitrile lyase (S)-hydroxynitrile lyase, which is a subject of immobilization, can be prepared by extraction from biological tissues(e.g. a plant tissue which contains the enzyme), or genetic engineering technology. It is preferable to prepare (S)-hydroxynitrile lyase by genetic engineering technology in terms of its stable supply. The preparation of (S)-hydroxynitrile lyase by genetic engineering technology can be performed as follows for example.

(1) Source of a Gene Encoding (S)-hydroxynitrile lyase

Examples of sources of a gene encoding (S)-hydroxynitrile lyase (also referred to as "(S)-hydroxynitrile lyase gene" hereinafter) include plants of Euphorbiaceae such as Manihot esculenta and Hevea brasiliensis, Poaceae (Gramineae) such as Sorghum bicolor, and Olacaceae such as Ximenia americana. In addition, all organisms containing (S)-hydroxynitrile lyase can be used as the source of the (S)-hydroxynitrile lyase gene.

(2) Cloning of (S)-hydroxynitrile lyase Gene

The (S)-hydroxynitrile lyase gene can be cloned from the sources of (1) above as follows. First, cDNA is prepared in the usual manner. On the other hand, primers for amplifying (S)-hydroxynitrile lyase gene by PCR is designed and synthesized based on the known nucleotide sequence of (S)-hydroxynitrile lyase gene. For example, primers for amplifying (S)-hydroxynitrile lyase gene derived from Manihot esculenta can be based on the nucleotide sequence described in "Arch. Biochem. Biophys. 311, 496–502 (1994)", as follows.

```
Sense primer:
5'-ggggaattcatggtaactgcacattttgttctgattc-3'
(SEQ ID NO:1)

Antisense primer:
5'-ggggtcgacctcacggattagaagccgccg-3'
(SEQ ID NO:2)
```

Then, the (S)-hydroxynitrile lyase gene is amplified by PCR with the synthesized primer for amplification, using cDNA prepared from organisms of (1) above in the usual manner as a template. After ligating the resulting PCR amplified fragment to an appropriate vector, the nucleotide sequence is confirmed, thereby regarding the one with the nucleotide sequence of (S)-hydroxynitrile lyase gene as a clone containing (S)-hydroxynitrile lyase gene.

(3) Construction of an (S)-hydroxynitrile lyase Expression Vector

Constructing an (S)-hydroxynitrile lyase expression vector can be performed by cutting out a region encoding (S)-hydroxynitrile lyase from the clone containing (S)-hydroxynitrile lyase gene obtained in (2) above, and ligating it to an appropriate expression vector. The expression vector as used herein is selected depending on host types to be used for expressing (S)-hydroxynitrile lyase protein. For example, in the case where an yeast *Saccharomyces cerevisiae* is used as a host, episome-type expression vectors including YEp51, YEp351 and pYES2 can be used, and in the case where *E. coli* is used as a host, expression vectors such as pKK223–3, pKK233–2 and pTrc99A can be used.

(4) Preparation of Transformant Containing (S)-hydroxynitrile lyase Gene

A transformant containing the (S)-hydroxynitrile lyase gene can be prepared by transforming the (S)-hydroxynitrile lyase gene expression vector obtained in (3) above to a host cell. In detail, the transformation of the yeast *Saccharomyces cerevisiae* can be carried out by such methods as electroporation, spheroplast method and lithium acetate method, and the transformation of *E. coli* can be carried out by such methods as calcium chloride method and electroporation. A desired transformant can be selected after the transforming operation by inoculating transformants on an appropriate selection medium and choosing a grown strain.

(5) Preparation of (S)-hydroxynitrile lyase Protein (S)-hydroxynitrile lyase protein can be obtained by culturing the transformant obtained in (4) above in a medium and collecting the culture. The culture as used herein, means any of a culture supernatant, or a cultured cell or microbial cell, or a disrupted material of the cultured cell or microbial cell. A method for culturing the transfortnant in a medium can be performed in a usual manner used for culturing a host.

For example, the medium for culturing a transformant obtained with yeast as a host is not particularly limited as far as an introduced (S)-hydroxynitrile lyase gene is maintained stably in the host, and at the same time, (S)-hydroxynitrile lyase is produced by gene expression in the host. It is preferable to adjust a carbon source and/or an amino acid composition and/or an additive composition to be used for culture depending on properties of a host and an introduced selective marker gene. The culture is continued until the production of (S)-hydroxynitrile lyase by microbial host cell is stopped under temperature and pH conditions where growth of the host is not inhibited (normally 30° C., pH 4–8).

When (S)-hydroxynitrile lyase protein is produced in the microbial cell after culture, the protein is extracted by destroying the microbial cell or cell. Furthermore, when the enzyme protein is produced outside of the microbial cell, the culture fluid may be used as is, or the microbial cell or cell is removed by centrifugation or the like. Then, the (S)-hydroxynitrile lyase protein can be purified from the culture using general biochemical methods to isolate and purify proteins, such as an ammonium sulfate precipitation, a gel chromatography, an ion exchange chromatography, an affinity chromatography, and a hydrophobic chromatography alone or optionally in combination.

2. Immobilization of (S)-hydroxynitrile lyase (1) Carrier for Immobilization of (S)-hydroxynitrile lyase Various carriers comprising porous inorganic materials can be used as the immobilization carrier for (S)-hydroxynitrile lyase. Examples of such carriers include sintered clay carriers, the silica carriers, the alumina carriers, and the silica alumina carriers.

The sintered clay carrier means a porous carrier obtained by granulating and sintering silicate raw materials (e.g. kaolinite-group minerals including kaolinite, dickite, nacrite and halloysite; and clays including pyrophyllite, montmorillonite, sericite, talc and chlorite). To be more specific, Toyonite200 (Toyo Denka Kogyo) and Toyonite200A (Toyo Denka Kogyo) are included.

The silica carrier means a porous carrier with a high surface area made of agglutinated micro particles of silicon dioxide. To be more specific, Micro Bead Silica Gel (Fuji Silysia Chemical) and Chromatography Silica Gel (Fuji Silysia Chemical) can be included.

The alumina carrier means a porous carrier containing an aluminum oxide as the main ingredient. To be more specific, NeoBead DL (Mizusawa Chemical) and γ-alumina KHA-34 (Sumitomo Chemical.) can be included.

The silica alumina carrier means a porous carrier having aluminum oxide and silicon dioxide as the main ingredients. To be more specific, MIZUKASIEVES Y-540 Y-type zeolite (Mizusawa Chemical), MIZUKASIEVES 13X-488 zeolite 13X (Mizusawa Chemical), HSZ-630H0A H-mordenite (Tosoh) and Na-mordenite (Catalysts & Chemical Industries) can be included.

It is preferable to select carriers having an effective pore size for immobilizing enzyme adequately, since the absorption (or adsorption) amount of the enzyme depends on a pore size of a porous inorganic material carrier as described above. To be more specific, the selected pore size is 10–80 nm, preferably 10–60 nm, and most preferably 10–40 nm. Morepver, the specific surface area of the porous inorganic material is preferred to be as large as possible in order to immobilize the enzyme as much as possible, specifically, it is preferred to be more than 20 $m^2/g$. A form of the carrier used for immobilization is not specifically limited as long as it is porosity, but is preferred to be spherical in the case where the immobilized enzyme for filling-type of reaction vessel is prepared. In considering workability to separate the immobilized enzyme, or pressure drop generated when fluid passes through the packed bed type reactor, a particle size is preferred to be, but is not limited to, 10 $\mu$m–5 mm, preferably 100 $\mu$–2 mm, having relatively narrow size distribution.

(2) Immobilization of (S)-hydroxynitrile lyase in Carrier

The immobilization of (S)-hydroxynitrile lyase in a carrier can be performed as follows. Solution containing (S)-hydroxynitrile lyase prepared as in (1) above is adjusted to a pH within the range of preserving enzyme activity, then it is mixed with the immobilization carrier of (1) above and stirred and left standing until the absorption ratio is maximized, thereby allowing the immobilization. Normally, the maximum absorption ratio is achieved when the solution is stirred and left standing for 6–24 hours. Still further, it is preferred to set the concentration of a salt low during immobilization, since the absorption of enzyme in the carrier tends to be inhibited as the concentration of a salt increases. For example, the concentration of a salt to be used during immobilization is 0.5M or lower, preferably 0.1M or lower. Then, after the immobilization treatment, the resulting immobilized enzyme can be separated by filtration or the like. Moreover, when water is contained in excess amounts in the immobilized enzyme, it can cause aggregation among carriers in the reaction solvent at the time of synthesizing optically active cyanohydrin, therefore it is preferred to remove water contained in the immobilized enzyme to its dispersible level. Water from the immobilized enzyme can be dried under reduced pressure or air-dried to be removed.

3. Synthesis of Optically Active Cyanohydrin Using the Immobilized Enzyme of the Present Invention.

Synthesis of an optically active cyanohydrin using the immobilized enzyme of the present invention can be performed as follows. At first, the immobilized enzyme obtained in (2) above and a reactive substrate are added to a reaction solvent, and the reaction was performed for 20 minutes to 24 hours at a reaction temperature of 10 to 50° C., thereby synthesizing the optically active cyanohydrin. The reaction time is adjusted appropriately depending on the conversion ratio of the substrate. After completion of the synthetic reaction, the immobilized enzymes are collected and used again for synthesizing the optically active cyanohydrin. As the reaction substrate, a carbonyl compound and a cyanogen compound can be used. The carbonyl compound as used herein, is an aldehyde or ketone, specifically represented by the formula (1):

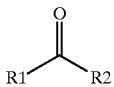

In the formula (1), R1 and R2 are (i) a hydrogen atom (ii) a substituted or unsubstituted $C_{1-18}$ linear or branched chain saturated alkyl group, or (iii) a substituted or unsubstituted 5–22 membered ring aromatic group. However, $R_1$ and $R_2$ are not hydrogen atoms at the same time.

In above (ii), where $R_1$ and $R_2$ are a substituted alkyl group, the substituent is one or more amino groups, imino groups, hydroxy groups, $C_{1-8}$ alkoxy groups, halogen, carboxyl groups, $C_{3-20}$ cycloalkyl groups, or aromatic groups having a carbon number not more than 22 in which the carbon atoms may be substituted by a hetero atom of N, O or S (When the substituent is a cyclic substituent, then it may be substituted by one or more halogen atoms, hydroxy groups, $C_{1-8}$ linear or branched chain alkyl groups, or $C_{2-8}$ linear or branched chain alkenyl groups).

In above (iii), the aromatic group may be a hetero aromatic group in which not more than 4 ring members are substituted by N, O and/or S. Still further, where $R_1$ and $R_2$ are a substituted aromatic group, the substituent is one or more amino groups, imino groups, hydroxy groups, $C_{1-8}$ alkoxy groups, allyloxy groups, harogen, carboxyl groups, or linear or branched chain saturated or unsaturated alkyl groups having a carbon number not more than 22 (wherein one aromatic group may be substituted by at least 2 substituents).

Furthermore, the cyanogen compound as a substrate which is added to the reaction system includes, but is not limited to, hydrocyanic acid salts such as sodium cyanide and potassium cyanide, and cyanohydrins such as acetone cyanohydrin as long as it generates a cyanide ion ($CN^-$).

Still further, in considering that racemization of an optically active cyanohydrin generated by the enzyme reaction tends to occur in the presence of large amounts of water in the reaction system, or that production efficiency decreases when aldehyde or ketone having a small solubility to water is used as a raw material, it is preferred to use a reaction solvent comprising a slightly water-soluble or water-insoluble organic solvent as a main ingredient. Such organic solvent can be used without any specific limitation as long as it does not affect the synthetic reaction of an optically active cyanohydrin using the enzyme, and can be selected appropriately depending on physical properties of the aldehyde or ketone to be used as a raw material for synthetic reaction, and/or physical properties of a product, cyanohydrin. To be more specific, examples of the reaction solvent are linear or branched or cyclic saturated or unsaturated aliphatic or aromatic hydrocarbon solvents which may be halogenated (e.g. pentane, hexane, toluene, xylene, dichloromethane, etc.); linear or branched or cyclic saturated or unsaturated aliphatic or aromatic alcohol solvents which may be halogenated (e.g. isopropyl alcohol, n-butanol, iso-butanol, t-butanol, hexanol, cyclohexanol, n-amyl alcohol, etc.); linear or branched or cyclic saturated or unsaturated aliphatic or aromatic ether solvents which may be halogenated (e.g. diethyl ether, dipropyl ether, diisopyl ether, dibutyl ether, methyl-t-butyl ether, etc.); linear or branched or cyclic saturated or unsaturated aliphatic or aromatic ester solvents which may be halogenated (e.g. methyl formate, methyl acetate, ethyl acetate, butyl acetate, methyl propionate, etc.), and these solvents can be used alone or in combination. The solvents used may contain water or an aqueous buffer or may be saturated therewith.

Furthermore, in the present invention, for the purpose of stabilizing the immobilized enzyme, either or both of treatments for decreasing an oxygen concentration in the synthetic reaction system of an optically active cyanohydrin, and for decreasing hydroquinone or compounds derived from hydroquinone (e.g. benzoquinone, quinhydrone, etc.) in the reaction system can be performed.

In the present invention, the treatment for decreasing the oxygen concentration in the reaction system means, to be more specific, the treatment for reducing a dissolved oxygen by bringing the reaction solvent into contact with a gas which does not affect the reaction (e.g. nitrogen, argon, helium, etc.), and substituting the gas for the dissolved oxygen in the reaction solvent. This treatment may be performed in the usual manner. For example, in this treatment the reaction solvent is put in a container with an agitator and is aerated with an inactive gas as described above to the liquid while agitating. Specifically, the treatment can be performed by aerating the inactive gas in an aeration volume of 1 ml to 10L per minute per liter of the reaction solvent for 1 min to 1 hour, preferably 10 ml to 5 L per minute per liter of the reaction solvent for 5 min to 30 min. It can also be performed by distilling the reaction solvent in an atmosphere of the inactive gas. It can also be performed by adding an deoxidizer such as a sodium sulfite and hydrosulfite. Furthermore, it can also be performed by causing the reaction while aerating the inactive gas in the gas phase of the reaction container in the aeration volume described above.

In the invention, the treatment for reducing the concentration of the hydroquinone and hydroquinone-derived compounds in the reaction system is performed by distilling the reaction solvent and separating it from hydroquinone or hydroquinone-derived compounds contained in the reaction solvent. The concentration of hydroquinone and hydroquinone-derived compounds is reduced to less than 40 ppm, preferably less than 1 ppm. The distillation may be carried out under normal pressure or reduced pressure in temperature conditions where hydroquinone and hydroquinone-derived compounds remain and only the reaction solvent is distilled away. Alternatively, the treatment can be performed by adding an adsorbing agent (e.g. activated carbon) into the reaction solvent contained hydroquinone and hydroquinone-derived compounds, or by passing the solvent through, for example, a column filled with the adsorbing agent, or by bringing the reaction solvent into contact with the adsorbing agent for a certain period of time according to other methods. In such case, the amount of the adsorbing agent can be determined appropriately depending on the adsorbing capacity of the agent.

Then, the generated optically active cyanohydrin can be measured and quantified by high performance liquid chromatography (HPLC) or the like.

EXAMPLES

Embodiments of the invention will be described below by means of illustration, but it is not intended that the scope of the invention is limited to them.

Example 1

Preparation of (S)-hydroxynitrile lyase (S)-hydroxynitrile lyase was prepared by genetic engineering technology using the yeast *Saccharomyces cerevisiae* as a host as follows. First of all, the total mRNA was extracted from the cassava (Manihot esculenta) leaf in the usual manner. Then, cDNA synthesis was performed to produce cDNA using the obtained mRNA as a template. On the other hand, the primers described below were synthesized based on the sequence of (S)-hydroxynitrile lyase gene derived from cassava described in "Arch. Biochem. Biophys. 311, 496–502 (1994)".

```
Sense primer:
ggggaattcatggtaactgcacattttgttctgattc
(SEQ ID NO:1)

Antisense primer:
ggggtcgacctcacggattagaagccgccg
(SEQ ID NO:2)
```

PCR was performed using above cDNA as a template with the synthesized primers (90° C., 30 sec; 55° C., 30 sec; 72° C., 60 sec; 35 cycles in total) to obtain (S)-hydroxynitrile lyase gene. Analysis of the gene sequence indicated that it was consistent with the sequence shown in the document.

Then, the yeast episomal expression vector YEp352-GC was prepared by inserting the obtained PCR fragment between the YEp352-GAP promoter and terminator. This vector was transformed with the yeast *Saccharomyces cerevisiae* Inv-Sc1 strain in the usual manner, and the recombinant yeast YEp352-GC-S2 strain containing the expression vector YEp352-GC was obtained by selecting a strain which proliferates in a minimum selection medium without uracil.

Then, the obtained recombinant yeast YEp352-GC-S2 strain was incubated for 24 hours in YNBDCas liquid medium (6.7 g/L Yeast nitrogen base without amino acid (Difco), 20 g/L glucose, 20 g/L casamino acid, 40 mg/mL L-tryptophan), thereby producing (S)-hydroxynitrile lyase in the cells. The microbial cells were collected from the culture broth of a recombinant fungus by centrifugation, and destroyed using a beads mill. The destroyed microbial cell suspension was centrifugated to prepare a crude extract, and this product crudely purified by ammonium sulfate fractionation was used as (S)-hydroxynitrile lyase solution for the following examples.

Example 2

Examination of (S)-hydroxynitrile lyase Immobilization Carrier (1) Immobilization on the Sintered Clay Carrier and the Silica Carrier (S)-hydroxynitrile lyase prepared as in example 1 was immobilized in the various enzyme immobilization carriers, and the type of carrier suitable for immobilizing the enzyme was examined. Immobilization of enzyme was performed by adding 0.1 g of various carriers to 0.5 ml of the (S)-hydroxynitrile lyase solution (activity: 64U/ml, 0.02M HEPES-Na buffer (pH6.0)) respectively, and agitating for 24 hours at 4° C., thereby allowing absorption and immpbilization of the enzyme protein in each carrier. Then, the absorption ratio of the enzyme protein in the carrier was examined. The absorption ration of the enzyme protein In the carrier was calculated by measuring a remaining (S)-hydroxynitrile lyase activity (residual activity) in a supernatant liquid after immobilization and (S)-hydroxynitrile lyase activity (control activity) in a control (an enzyme mixture without the carrier), and substituting the measured values into the following formula. The results are shown in Table 1. Enzyme activity was calculated by measuring at a wavelength of 249.6 nm changes in absorbance of light when DL-Mandelonitrile as a substrate is decomposed by the enzyme to generate benzaldehyde. One unit (U) of activity was defined as equivalent to the generation of 1 μmol of benzaldehyde per minute.

$$\text{Adsorption Ratio (\%)} = \frac{\text{Control Activity} - \text{Residual Activity}}{\text{Residual Activity}} \times 100 \quad \text{Formula (1)}$$

TABLE 1

Absorption ratio of enzyme to various immobilization carriers

| Immobilization carrier | Material | Residual activity (U/ml) | Absorption Ratio (%) |
|---|---|---|---|
| Toyanite 200 (Toyo Denka Kogyo) | sintered clay | 0 | 100 |
| Choromatography Silica Gel FL60D (Fuji Silysia Chemical) | silica | 0.071 | 99.88 |
| Avicel Cellulose Microcristalline (Merck) | cellulosic | 48.63 | 20.19 |
| Cellulose w-200G (Nippon Paper Industries) | cellulosic | 54.99 | 9.75 |
| Control | — | 60.93 | — |

While the absorption ratios on cellulosic immobilization carriers previously known as immobilization carriers for (S)-hydroxynitrile lyase were 20.19%, shown by Avicel Cellulose Microcristalline (Merck), and 9.75% by Cellulose w-200G (Nippon Paper Industries), the absorption ratio on Toyonite 200 (Toyo Denka Kogyo) of the sintered clay carrier was 100%, and the absorption ratio on Chromatography Silica Gel FL60D (Fuji Silysia Chemical) was 99.88%.

(2) Immobilization in the Carrier Comprising other Porous Inorganic Materials

Immobilization of (S)-hydroxynitrile lyase in a carrier comprising a broader range of porous inorganic materials was examined. Immobilization of the enzyme was performed in the same procedures as in (1) above. That is, 0.1 g of each carrier was added to 1 ml of the (S)-hydroxynitrile lyase solution (activity: 35U/ml, 0.02M HEPES-Na buffer (pH6.0)), followed by agitation for 24 hours at 4° C., thereby allowing absorption and immobilization of the enzyme protein on each carrier Then, the absorption ratio of the enzyme protein on the carrier was examined. The results are shown in Table 2.

TABLE 2

Absorption ratio of enzyme in various immobilization carriers

| Immobilization carrier | Material | Residual activity (U/ml) | Absorption Ratio (%) |
|---|---|---|---|
| Toyonite 200 (Toyo Denka Kogyo) | sintered clay | 7.43 | 75.25 |
| Choromatography Silica Gel FL60D (Fuji Silysia Chemical) | silica | 4.17 | 86.11 |
| Micro Bead Silica Gel 300A (Fuji Silysia Chemical) | silica | 2.895 | 90.35 |
| γ-Alumina KHA-34 (Sumitomo Chemical.) | alumina | 18.23 | 39.23 |
| NeoBead DL (Mizusawa Chemical) | alumina | 16.08 | 46.40 |
| MIZUKASIEVES 13X-488 zeolite 13X (Mizusawa Chemical) | silica alumina | 17.80 | 40.66 |
| MIZUKASIEVES Y-540 Y-type zeolite (Mizusawa Chemical) | silica alumina | 16.07 | 46.45 |
| HSZ-630HOA H-mordenite (Tosoh) | silica alumina | 16.47 | 45.10 |
| Na-mordenite (Catalysts & Chemical Industries) | silica alumina | 18.57 | 38.09 |
| XZ-16052 $ZrO_2$ (Norton) | $ZrO_2$ | 20.11 | 32.96 |
| XT-25376 $TiO_2$ (Norton) | $TiO_2$ | 15.94 | 46.85 |
| Control | — | 30.01 | — |

The absorption ratio of the alumina carrier to NeoBead DL (Mizusawa Chemical) was 46.4%, and the counterpart to MIZUKASIEVES Y-540 Y-type zeolite (Mizusawa Chemical) was 46.45%. Thus, an alumina carrier and silica alumina carrier were found as immobilization carriers having higher absorption ratios than previous cellulosic carriers.

Example 3

Effect of the Pore Size on the Absorption Ratio of the Enzyme

The relation between the pore size of a carrier and the absorption ratio of the enzyme was examined using Toyonite200, a sintered clay carrier and Micro Bead Silica Gel, a silica carrier. Immobilization of the enzyme was performed in the same manner as in (1) above. That is, 0.05 g of each carrier was added to 1 ml of the (S)-hydroxynitrile lyase solution (activity: 50U/ml, 0.02M HEPES-Na buffer (pH6.0)), followed by agitation for 24 hours at 4° C., thereby allowing absorption and immobilization of the enzyme protein in each carrier. Then, the absorption ratio of the enzyme protein in the carrier was examined. The results in the case where Toyonite200 was used are shown in Table 3 and FIG. 1, and the results in the case where Micro Bead Silica Gel was used are shown in Table 4 and FIG. 2.

TABLE 3

Effect of pore size on the absorption ratio on Toyonite 200

| Immobilization carrier | Pore size (nm) | Surface area (m²/g) | Residual activity (U/ml) | Absorption ratio (%) |
|---|---|---|---|---|
| Toyonite 200 | 28 | 120 | 29.4 | 31.9 |
| Toyonite 200 | 38 | 97 | 22.3 | 48.4 |
| Toyonite 200 | 60 | 43 | 26.6 | 38.2 |
| Toyonite 200 | 72 | 25 | 31.6 | 26.7 |
| Control | — | — | 43.1 | — |

TABLE 4

Effect of pore size on the absorption ratio on Micro Bead Silica Gel

| Immobilization carrier | Pore size (nm) | Surface area (m²/g) | Residual activity (U/ml) | Absorption ratio (%) |
|---|---|---|---|---|
| Micro Bead Silica Gel 4B | 7 | 500 | 34.2 | 20.7 |
| Micro Bead Silica Gel 150A | 16.4 | 196 | 27.5 | 36.3 |
| Micro Bead Silica Gel 5D | 18.9 | 250 | 22.4 | 48.0 |
| Micro Bead Silica Gel 200A | 20 | 169 | 17.2 | 60.2 |
| Micro Bead Silica Gel 300A | 30 | 112 | 18.0 | 58.2 |
| Micro Bead Silica Gel 500A | 50 | 69 | 24.6 | 42.9 |
| Micro Bead Silica Gel 800A | 80 | 47 | 31.4 | 27.3 |
| Micro Bead Silica Gel 1000A | 100 | 43 | 32.3 | 25.2 |
| Control | — | — | 43.1 | — |

Figure 2:
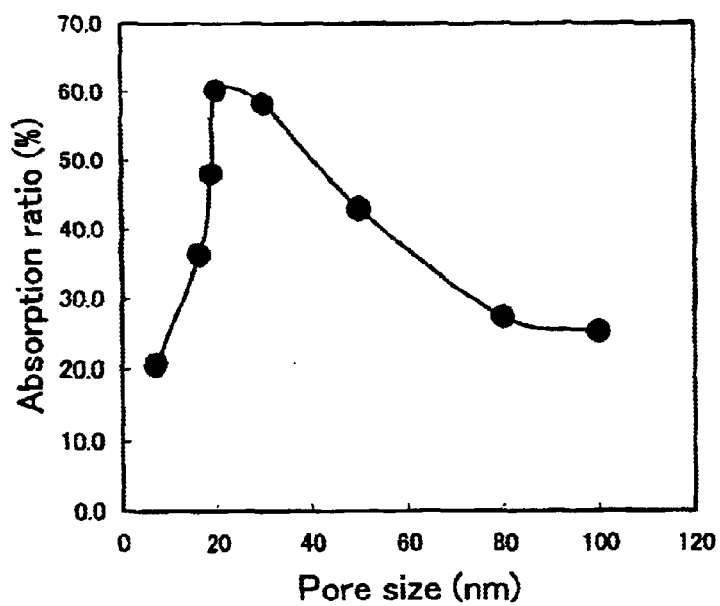
FIG. 2 shows the effect of the pore size of an immobilization carrier on the absorption ratio of enzyme in the case where Micro Bead Silica Gel is used as the carrier.

As is obvious from Table 3 and FIG. 1, relatively high absorption ratios were obtained with a pore size ranging from 28 to 60 nm in the case of the Toyonite200, sintered clay carrier, and among them, the highest absorption ratio was obtained at around 38 nm. Relatively high absorption ratios were obtained with a pore size ranging from 18.9 to 50 nm in the case of Micro Bead Silica Gel, a silica carrier, and among them, the highest absorption ratio was obtained at around 20 nm.

Example 4

Effect of pH at the Time of Immobilization on the Absorption Ratio of the Enzyme and the Yield of the Optically Active Cyanohydrin The effect of pH at the time of immobilization on the absorption ratio of enzyme and the yield of the optically active cyanohydrin were examined using Micro Bead Silica Gel 300A, silica carrier as the immobilization carrier. At first, 0.05 g of each carrier was added to 1 ml of a citrate-phosphate buffer containing (S)-hydroxynitrile lyase (activity: 50U/ml), which was adjusted to various pH ranging from pH 3.81 to pH 7.73, subsequently, it was agitated for 24 hours at 4° C., thereby adsorbing and immobilizing the enzyme protein in each carrier. Then, the absorption ratio was examined as in the same manner previously mentioned.

Subsequently, the immobilized enzyme prepared at each pH was collected by filtration, then it was washed with 0.15M of sodium citrate buffer (pH5.0), and left until the immobilized enzyme became dry and loosened. 2.5 ml of ethylacetate as a reaction solvent and 99 μl of 3-phenoxybenzaldehyde (0.5 mmol) and 57 μl of prussic acid (1.5 mmol) as a substrate were added to the obtained immobilized enzyme, subsequently, the synthetic reaction of the optically active cyanohydrin was performed by rotating a roller bottle with the reaction mixture at room temperature. After the completion of the reaction, the amount of the generated (S)-3-phenoxybenzaldehyde cyanohydrin was measured by HPLC. The absorption ratio and the relative reactivity are shown in Table 5 and FIG. 3, wherein the HPLC peak area that corresponds to the maximum amount of (S)-3-phenoxybenzaldehyde cyanohydrin formed at pH 5.44 is taken as 100,.

TABLE 5

Effect of pH at the time of enzyme immobilization on the absorption ratio and the yield of optically active cyanohydrin

| pH | Residual activity (U/ml) | Absorption ratio (%) | Reactivity (%) |
|---|---|---|---|
| 3.81 | 13.71 | 44.97 | 5.22 |
| 4.33 | 7.89 | 68.32 | 36.59 |
| 4.83 | 5.66 | 77.26 | 52.22 |
| 5.44 | 5.35 | 78.52 | 100.00 |
| 5.95 | 5.39 | 78.36 | 78.10 |
| 6.40 | 5.23 | 79.01 | 76.21 |
| 6.79 | 5.92 | 76.24 | 47.97 |
| 7.23 | 7.37 | 70.42 | 26.65 |
| 7.55 | 14.5 | 41.79 | 11.36 |
| 7.73 | 16.02 | 35.70 | 4.26 |
| Control | 49.82 | — | — |

Figure 3:
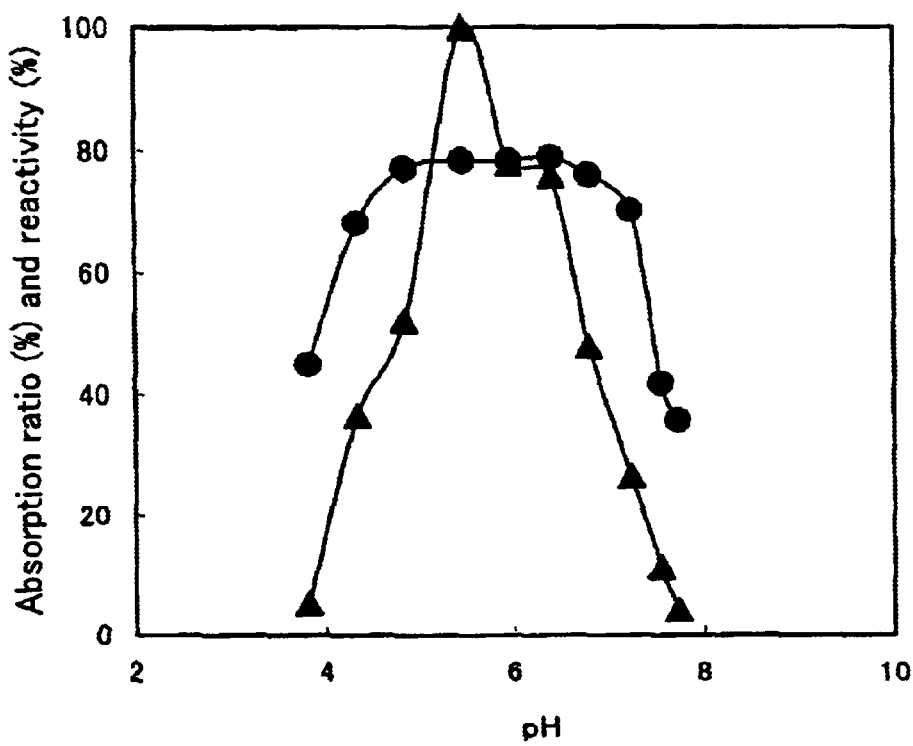
FIG. 3 shows the effect of pH on the absorption ratio and reactivity of enzyme in the case where Micro Bead Silica Gel 300A is used as the immobilization carrier.

As is obvious from Table 5 and FIG. 3, the absorption ratio on Micro Bead Silica Gel 300A was favorable in relatively broad range of pH 4.83–6.79, and the maximum value for the yield was shown at pH 5.5.

Example 5

Effect of the Buffer Concentration at the Time of Immobilization on the Absorption Ratio of the Enzyme The effect of the buffer concentration at the time of immobilization on the absorption ratio of the enzyme was examined using Micro Bead Silica Gel 300A, silica carrier as the immobilization carrier. 0.05 g of each carrier was added to 1 ml of a citrate-phosphate buffer containing (S)-hydroxynitrile lyase (activity: 50U/ml) which was adjusted to various concentration ranging from 0.02 to 0.5M, followed by agitation for 24 hours at 4° C., thereby allowing absorption and immobilization of the enzyme protein in each carrier. Then, the absorption ratio of the enzyme protein in the carrier was examined as in the same manner previously described. The results are shown in Table 6 and FIG. 4.

TABLE 6

Effect of buffer concentration at the time of immobilizing enzyme on the absorption ratio

| Buffer concentration (M) | Residual activity (U/ml) | Absorption ratio (%) |
|---|---|---|
| 0.02 | 22.14 | 48.68 |
| 0.05 | 25.37 | 41.19 |
| 0.1 | 26.27 | 39.10 |
| 0.5 | 32.93 | 23.67 |
| Control | 43.14 | — |

Figure 4:
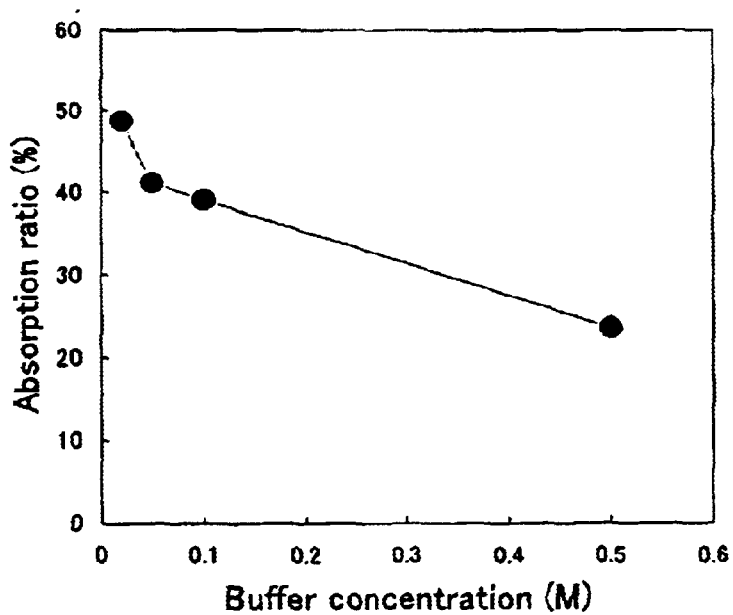
FIG. 4 shows the effect of the concentration of a buffer on the absorption ratio of enzyme in the case where Micro Bead Silica Gel 300A is used as the immobilization carrier.

As is obvious from Table 6 and FIG. 4, it was found out that the absorption ratio was highest at 0.02M, and furthermore, the lower the concentration of a buffer was at the time of immobilization of the enzyme, the higher the absorption ratio became.

Example 6

Synthetic Reaction which was Treated to Reduce the Oxygen Concentration and the Hydroquinone Concentration in the Reaction System After removing hydroquinone by distillation, the synthesis of (S)-3-phenoxybenzaldehyde cyanohydrin was performed using diisopropyl ether which was purged and deoxygenated by nitrogen.

235.8 ml of diisopropyl ether, 11.9 g of 3-phenoxybenzaldehyde aldehyde, 64 ml of hydrogen cyanide-diisopropyl ether solution (37.85 g HCN/500 ml) were added to the immobilized enzyme prepared in the same manner as in example 2 using Toyonite 200, the sintered clay carrier as the immobilizing carrier, and then it was followed by agitation at 25° C.

Figure 5:
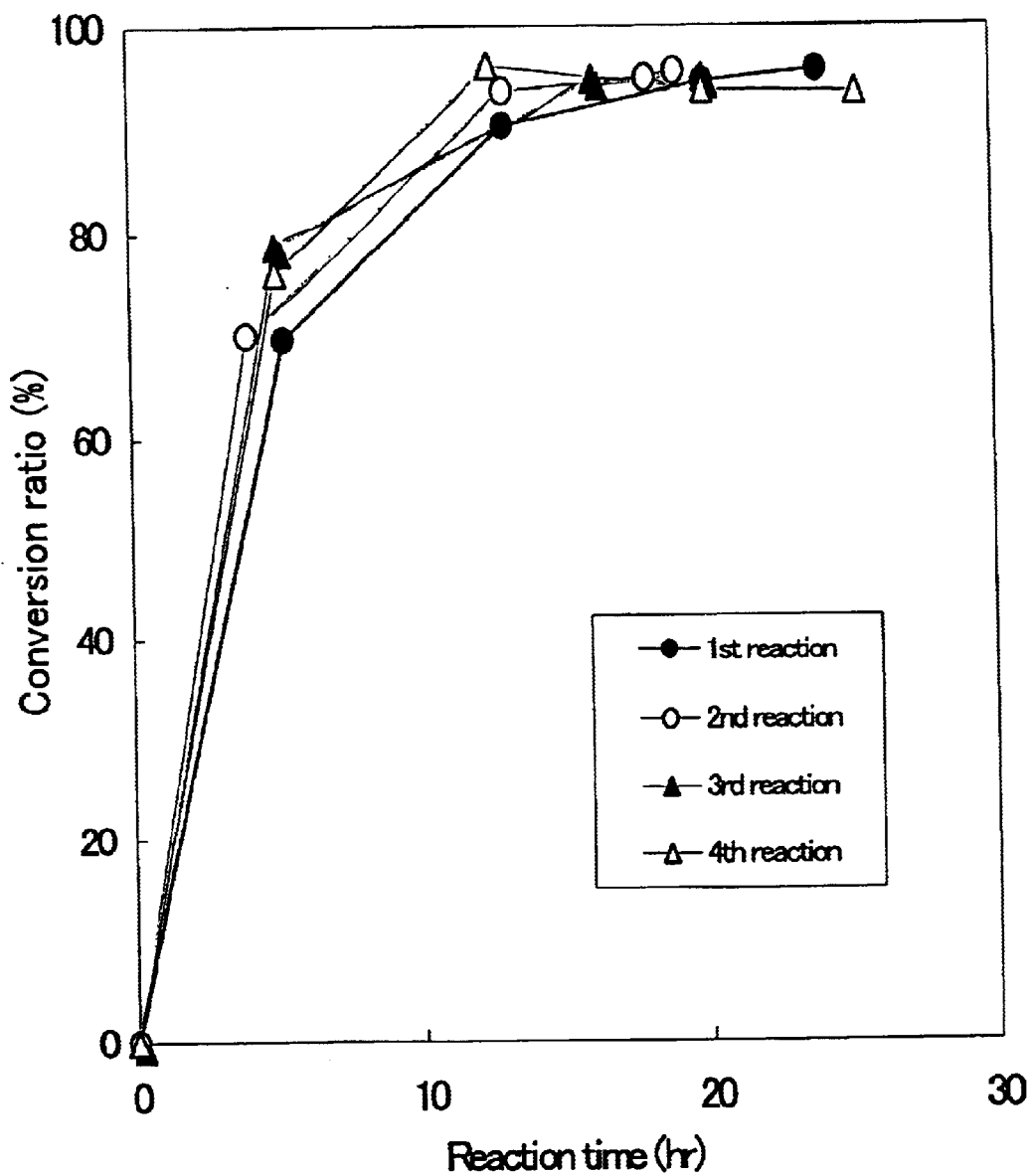
FIG. 5 shows changes in conversion ratio in each reaction cycle.

The immobilized enzyme was separated when the reaction was almost completed, then solvent and substrate of the same quantity as in the above were added to perform the reaction repeatedly. As shown in FIG. 5, reduction in the reaction rate was not observed even when the reaction was repeated 4 times. Furthermore, the conversion ratio and the optical purity of the generated (S)-3-phenoxybenzaldehyde when each reaction was completed, are shown in Table 7. From these results, it can be considered that there was no reduction in optical purity.

TABLE 7

Conversion ratio and optical purity in each reaction cycle

| Reaction cycle | Reaction time (hrs.) | Conversion ratio (%) | Optical purity (% ee) |
|---|---|---|---|
| 1st | 24 | 95.8 | 98.16 |
| 2nd | 19 | 95.7 | 98.33 |
| 3rd | 20 | 95 | 98.26 |
| 4th | 25.35 | 93.7 | 97.73 |

Example 7

Reusability of the Immobilized Enzyme 1.5 g of Micro Bead Silica Gel 200A (pore size: 20 nm) was added to 14 ml of (S)-hydroxynitrile lyase solution (activity: 43U/ml) obtained in the method as in example 1, then agitating gently, thereby allowing the immobilization of the enzyme. The immobilized enzymes were collected by filtration, and the excess amount of water was air-dried to be removed. 5 ml of t-butyl methyl ether containing 1.5M of hydrogen cyanide to this immobilized enzyme, subsequently benzaldehyde was added until the concentration became to 1M. The synthesis of (S)-mandelonitrile was performed by stirring and mixing it at room temperature. After the reaction was completed, the immobilized enzymes and the reaction solution were separated and the reaction solution was analyzed by HPLC. The analysis indicated that at 1.5 hours after starting the reaction, (S)-mandelonitrile having an optical purity not less than 99.9% ee was obtained at the conversion ratio 97.8% of benzaldehyde. Solvent and substrate of the same quantity as previously mentioned, were added to the separated immobilized enzyme to perform the reaction repeatedly. The results are shown in Table 8. As shown in Table 8, the high conversion ratio and high optical purity of the generated (S)-mandelonitrile were maintained in spite of the repeated reactions. As shown in the above description, it was found out that the immobilized enzyme of the invention is reusable and highly stable to a great extent in the synthetic reaction of optically active cyanohydrins.

TABLE 8

Conversion ratio and optical purity in each reaction cycle

| Reaction cycle | Reaction time (hrs.) | Conversion ratio (%) | Optical purity (% ee) |
|---|---|---|---|
| 1st | 1.5 | 98.7 | >99.9 |
| 2nd | 2.5 | 96.9 | 98.7 |
| 3rd | 3.0 | 97.9 | 99.1 |
| 4th | 2.5 | 97.7 | 99.2 |
| 5th | 2.5 | 98.0 | 99.1 |

ADVANTAGE OF THE INVENTION

The present invention provides an immobilized enzyme in which (S)-hydroxynitrile lyase is immobilized at high absorption ratio, a method for producing the immobilized enzyme, and a method for producing optically active cyanohydrins using the immobilized enzymes.

This specification includes part or all of the contents as disclosed in the specification and/or drawings of Japanese Patent Application No.2000–3386, which is priority documents of the present application.

Free-text of sequence listing

SEQ ID NO:1: synthesis DNA

SEQ ID NO:2: synthesis DNA

What is claimed is:

1. An immobilized Euphorbiaceae, Poaceae, or Olacaceae (S)-hydroxynitrile lyase enzyme immobilized by adsorption on a porous inorganic carrier.

2. The immobilized enzyme according to claim 1, wherein said porous inorganic carrier is selected from a sintered clay carrier, a silica carrier, an alumina carrier and a silica alumina carrier.

3. The immobilized enzyme according to claim 1, or 2, wherein said porous inorganic has a pore size of 10–80 nm.

4. The immobilized enzyme according to claim 1, or 2, wherein said porous inorganic carrier has a pore size of 10–60 nm.

5. The immobilized enzyme according to claim 1, or 2, wherein the surface area of the porous inorganic carrier is more than 20 $m^2/g$.

6. The immobilized enzyme according to claim 1, or 2, wherein the pH at the time of enzyme adsorption is between 4.83 and 6.79.

7. A method for producing an immobilized enzyme, comprising adsorbing an Euphorbiaceae, Poaceae, or Olacaceae (S)-hydroxynitrile lyase enzyme on a porous inorganic carrier.

8. The method for producing an immobilized enzyme according to claim 7, wherein said porous inorganic carrier is selected from a sintered clay carrier, a silica carrier, an alumina carrier and a silica alumina carrier.

9. The method for producing an immobilized enzyme according to claim 7 or 8, wherein said porous inorganic carrier has a pore size of 10–80 nm.

10. The method for producing an immobilized enzyme according to claim 7 or 8, wherein said porous inorganic carrier has a pore size of 10–60 nm.

11. The method for producing an immobilized enzyme according to claim 7 or 8, wherein surface area of the porous inorganic carrier is more than 20 $m^2/g$.

12. The method for producing an immobilized enzyme according to claim 7 or 8, wherein the pH at the time of enzyme adsorption is between 4.83 and 6.79.

* * * * *

UNITED STATES PATENT AND TRADEMARK OFFICE
CERTIFICATE OF CORRECTION

PATENT NO.    : 6,709,847 B2
DATED         : March 23, 2004
INVENTOR(S)   : Hisashi Semba et al.

It is certified that error appears in the above-identified patent and that said Letters Patent is hereby corrected as shown below:

Title page,
Item [54], Title, "IMMOBILIZED EUPHORBIACEAE, POACEAE OR OLACAEAE S-HYDROXYNITRILE LYASE." should read -- METHOD FOR SYNTHESIZING AN OPTICALLY ACTIVE CYANOHYDRIN --.

Column 14,
Lines 1, 3, 6 and 9, "claim 1, or 2," should read -- claim 1 or 2, --.
Line 2, "inorganic has" should read -- inorganic carrier has --.
Line 26, "wherein surface" should read -- wherein the surface --.

Signed and Sealed this

Twenty-fifth Day of January, 2005

JON W. DUDAS
*Director of the United States Patent and Trademark Office*

SEQUENCE LISTING

<160> NUMBER OF SEQ ID NOS: 2

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 1
ggggaattca tggtaactgc acattttgtt ctgattc          37

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 2
ggggtcgacc tcacggatta gaagccgccg          30